United States Patent [19]

Yamada

[11] Patent Number: 4,505,806
[45] Date of Patent: Mar. 19, 1985

[54] OXYGEN SENSOR

[75] Inventor: Tetsusyo Yamada, Nagoya, Japan

[73] Assignee: NGK Spark Plug Co., Ltd., Nagoya, Japan

[21] Appl. No.: 404,836

[22] Filed: Aug. 3, 1982

[30] Foreign Application Priority Data

Dec. 21, 1981 [JP] Japan ............................ 56-190419[U]

[51] Int. Cl.³ .......................................... G01N 27/46
[52] U.S. Cl. .................................... 204/425; 204/426; 204/427; 29/620; 156/89; 264/61; 427/126.5
[58] Field of Search ................. 204/424–429

[56] References Cited

U.S. PATENT DOCUMENTS

| 2,791,937 | 2/1974 | Besson et al. | 204/427 |
| 4,264,425 | 4/1981 | Kimura et al. | 204/429 |
| 4,272,329 | 6/1981 | Hetrick et al. | 204/1 T |
| 4,300,991 | 11/1981 | Chiba et al. | 204/426 |
| 4,359,989 | 11/1982 | Masaki et al. | 204/428 |

FOREIGN PATENT DOCUMENTS 56-130649 10/1981 Japan .

Primary Examiner—T. Tung
Attorney, Agent, or Firm—Fleit, Jacobson, Cohn & Price

[57] ABSTRACT

The disclosed oxygen sensor comprises a plate-like oxygen pump element with electrodes, a plate-like oxygen concentration cell element having electrodes disposed in parallel alignment with those of said pump element, and an intermediate board disposed between said two elements and having a hole defining a cavity between electrodes of said two elements, said intermediate board further having passages bored therethrough so as to communicate said cavity to outside of said oxygen sensor.

13 Claims, 9 Drawing Figures

OXYGEN SENSOR

BACKGROUND OF THE INVENTION

1. Field of the Invention

This invention relates to an oxygen sensor for measuring the oxygen concentration in a gas being measured such as an exhaust gas, and more particularly to an oxygen sensor which can very accurately determine the air-fuel ratio or the like of a gas being measured over a wide range.

2. Description of the Prior Art

To improve the fuel cost and the cleanness of exhaust gas of an automobile engine, it has been proposed to run the engine with an intake air-fuel mixture of lean burn side, i.e., with an air-fuel ratio $\lambda$, or an excess air ratio, larger than the theoretical optimal value at unity ($\lambda = 1$). To this end there is a need for an oxygen sensor which can accurately measure the air-fuel ratio of unity or larger than unity $\lambda \geq 1$. One example of such oxygen sensors of the prior art was disclosed in Japanese Patent Laying-open Publication No. 1380,649/81 which was filed by the Ford Motor Company of the U.S.A.

The above-mentioned Ford's oxygen sensor uses two sintered plates of oxygen-ion-conductive solid electrolyte each of which has electrodes attached to opposite surfaces thereof. One of the sintered plates is used as an oxygen pump element while the other one of them is used as an oxygen concentration cell element. The oxygen pump element and the oxygen concentration cell element are attached to opposite surfaces of a cylindrical spacer so as to sandwich the sidewall of the cylindrical spacer by the two elements. The sidewall of the cylinder spacer is made of a refractory material and has fine holes bored therein, so that an enclosed space is defined between the above-mentioned two elements while oxygen-diffusing holes are defined by said fine holes of the sidewall of the cylindrical spacer. The oxygen concentration of a gas can be electrically measured by placing the oxygen sensor in the gas and applying an electric current through the oxygen pump element so as to pump out the oxygen from the above-mentioned enclosed space to the outside atmosphere or the gas being measured while allowing diffusion of oxygen into the enclosed space through the oxygen-diffusing holes of the cylindrical spacer sidewall, until for instance an oxygen concentration ratio between the enclosed space and the outside atmosphere or the gas being measured reaches a certain stable value. The last mentioned oxygen concentration ratio is given by the oxygen concentration cell element as an output thereof, and the magnitude of the current applied to the oxygen pump element for pumping out oxygen corresponds to the oxygen concentration in the outside atmosphere or the gas being measured. This oxygen sensor uses the oxygen pump element and the oxygen concentration cell element which are separately formed, so that the output from the oxygen sensor has an advantage in that the dependency of the output thereof on the temperature of the outside atmosphere or the gas being measured is low.

However, the above-mentioned sensor of the prior art has shortcomings in that the material of the spacer is different from that of the two elements, that the coupling of the spacer with the two elements is made with adhesive of glass system or ceramic system and such coupling is weak against thermal shock and easy to peel off, and that the enclosed space is hard to keep airtight because of the difference of materials and the weak coupling. Thus, the oxygen sensor of the prior art is not quite satisfactory from the standpoint of the ease of manufacture and structural strength.

SUMMARY OF THE INVENTION

Therefore, an object of the present invention is to obviate the above-mentioned shortcomings of the oxygen sensors of the prior art such as the conventional oxygen sensors for measuring the air-fuel ratio, by providing a novel oxygen sensor which is easy to manufacture and yet has a high durability.

Another object of the invention is to provide an oxygen sensor having oxygen-diffusing holes which are free from clogging.

A still further object of the invention is to provide an oxygen sensor whose power consumption is small.

To fulfill the objects, an oxygen sensor according to the present invention comprises an oxygen pump element formed of a first oxygen-ion-conductive solid electrolyte board having electrode layers attached to opposite surfaces at one end of the first board and lead wire layers extending from said electrode layers to opposite end of the first board; an oxygen concentration cell element formed of a second oxygen-ion-conductive solid electrolyte board disposed in parallel to said first board, said second board having electrode layers attached to opposite surfaces at one end thereof in alignment with said electrode layers of said first board and lead wire layers extending from said electrode layers attached thereon to opposite end thereof; and a ceramic intermediate board member disposed between said oxygen pump element and said oxygen concentration cell element, said intermediate board member having a hole bored therethrough so as to define a cavity by closing said hole with said electrode layers attached to opposing surfaces of the first board and the second board, and at least one passage bored through said intermediate board member so as to communicate said cavity to outside of said oxygen sensor.

The intermediate board member may be made of either the same material as that of the first and second boards or a ceramic insulating material such as alumina or spinel.

In a preferred embodiment of the invention, the electrode layers and lead wire layers are formed by thick film forming technique, for instance by printing such layers with a paste containing heat-resisting metal and sintering the thus printed layers.

In another embodiment of the invention, a heat-generating resistor is embedded in the intermediate board member around the hole thereof, so as to selectively heat the oxygen sensor.

BRIEF DESCRIPTION OF THE DRAWINGS

For a better understanding of the invention, reference is made to the accompanying drawings, in which.

Throughout different views of the drawings, 1 is an oxygen pump element, 2 and 5 are solid electrolyte boards, 3a and 6a are electrode layers, 3b and 6b are lead wire layers, 4 is an oxygen concentration cell element, 7 is an intermediate board member, 8 is a hole, 9 is a passage, 10 and 10' are outside lead wires, 11 is a front portion, 12 is a rear portion, 13 and 13' are card-shaped body, 14 is a fixing hole, 15 is a cutting line, 16 is a heat-resisting metallic layer, 17 is a variable resistor, 18 is a volt meter and 19 is a direct power source.

DESCRIPTION OF THE PREFERRED EMBODIMENTS

Figure 1:
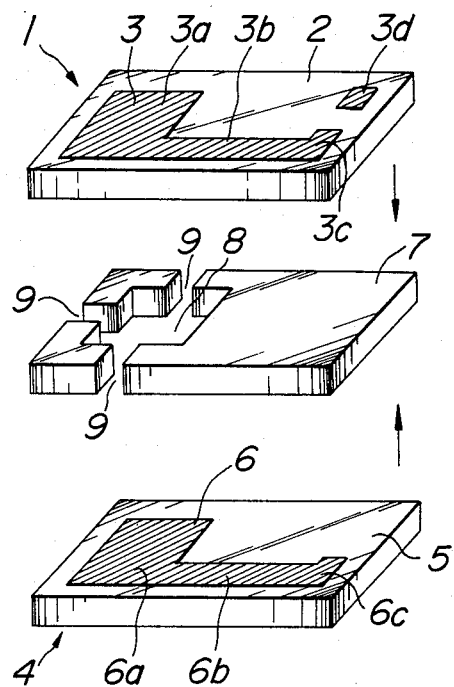
FIG. 1 is an exploded perspective view of a first embodiment of the oxygen sensor according to the present invention.

Referring to FIG. 1 showing an exploded perspective view of a first embodiment of the oxygen sensor according to the present invention, an oxygen pump element 1 has an oxygen-ion-conductive solid electrolyte board 2 with a porosity of 0–10% and a thickness of 0.5 mm, but the thickness can be in a range of 0.1–2.0 mm. The material of the solid electrolyte board 2 is, for instance, zirconium dioxide ($ZrO_2$) or thorium oxide ($ThO_2$), which is stabilized or partially stabilized with yttria ($Y_2O_3$), quick lime (CaO), or magnesia (MgO). Metallic layers 3 are attached to opposite surfaces of the solid electrolyte board 2, e.g., by conventional thick film forming technique, so that each of the metallic layers includes an electrode layer 3a, a lead wire layer 3b, and an outlet portion 3c or 3d. The metallic layer 3 is made of a heat-resisting metal such as platinum (Pt), ruthenium (Ru), palladium (Pd) rhodium (Rh), iridium (Ir), gold (Au), or silver (Ag), and platinum (Pt) is used in the illustrated example. The lead wire portion 3b connects the outlet portion 3c to the corresponding electrode layer 3a, and the outlet portion 3d is connected to the heat-resisting metallic layer 3 at the opposite side surface of the solid electrolyte board 2 by platinum paste filled in a hole (not shown) bored through the solid electrolyte board 2.

An oxygen concentration cell element 4 has an oxygen-ion-conductive solid electrolyte board 5 with the same shape and chemical composition as those of the solid electrolyte board 2 of the oxygen pump element 1. A pair of heat-resisting metallic layers 6 are attached to opposite surfaces of the solid electrolyte board 5, for instance by the thick film forming technique. Each of the metallic layers 6 has an electrode layer 6a, a lead wire layer 6b, and an outlet portion 6c or 6d (6d corresponding to 3d but not shown).

Preferably, each of the heat-resisting metallic layer 3 and 6 has a thickness of 5–20 μm and a porosity of 10–40%, because such thickness ensures a high electric conductivity in a direction parallel to the electrode layer and such porosity ensures good mobility of oxygen gas relative to the surface of the solid electrolyte board 2 or 5. The inventors used a porosimeter with pressurized mercury sealed therein for the measurement of the porosity.

An intermediate board member 7 is sandwiched between the oxygen pump element 1 and the oxygen concentration cell element 4. In the illustrated embodiment, the intermediate board member 7 is made of the same material as that of the solid electrolyte boards 2 and 5 and has an ultimate thickness of 0.5 mm, but the ultimate thickness can be in a range of about 0.1–2.0 mm. No electrode layers are provided on the intermediate board member 7, but a comparatively large hole 8 is bored through the entire thickness of the intermediate board member 7 at a position corresponding to both the electrode layer 3a of the oxygen pump element 1 and the electrode layer 6a of the oxygen concentration cell element 4. A plurality of comparatively small holes or passages 9 are bored through the intermediate board member 7, so as to communicate the comparatively large hole 8 to the outer edge periphery of the board member 7, as shown in FIG. 1. In the illustrated embodiment, three such passages 9 are bored, each of which is bored through the entire thickness of the intermediate board member 7. Thus, in a cross section of the passage 9 taken at right angles to the direction of communication between the hole 8 and the outer edge periphery of the board member 7, the height of the cross section is equivalent to the thickness of the intermediate board member 7. Such cross section provides a high response characteristics and prevents both clogging of the passages 9 with combustion residues carried by the exhaust gas and deterioration of the performance of the oxygen sensor due to such clogging. The total cross-sectional area of all such passages 9 is preferably larger than 1 $mm^2$, and more preferably larger than 3 $mm^2$, in terms of the ultimate areas thereof. If the above-mentioned total cross-sectional area is smaller than 1 $mm^2$, the response characteristics of the oxygen sensor is considerably reduced and the passages 9 become susceptible to clogging. In the illustrated example, each of the three passages 9 has a cross section of 0.5 mm × 2 mm and a length of 1 mm.

Figure 2:
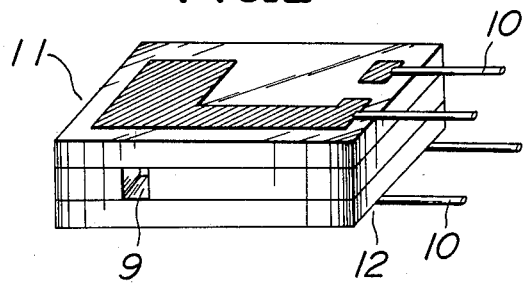
FIG. 2 is an overall perspective view of the assembled oxygen sensor of the first embodiment.

Referring to FIG. 2 showing a perspective view of the assembled oxygen sensor of the first embodiment, each passage 9 of the intermediate board member 7 gives an opening on the sidewall of the oxygen sensor so as to communicate a cavity defined by the hole 8 to the outside of the oxygen sensor. The front portion 11 of the oxygen sensor has a flat edge surface, but its rear portion 12 has outside lead wires 10 which are brazed to the outlet portions, e.g., 3c, 3d, 6c and 6d, of the metallic layers 3 and 6.

Figure 4:
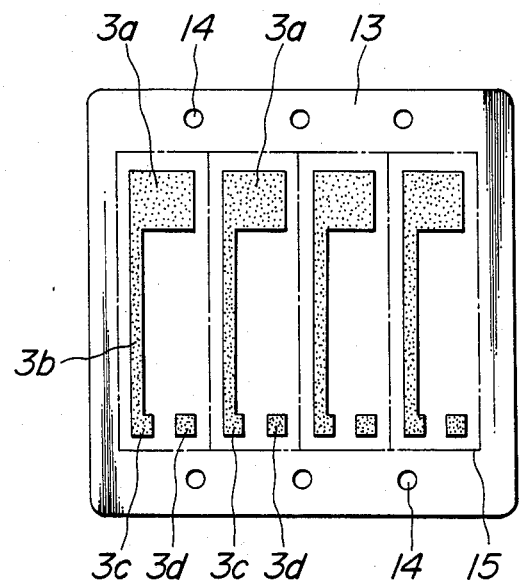
FIG. 4 is a plan view of a card-shaped body for a plurality of solid electrolyte boards of the oxygen pump element or oxygen concentration cell element, which body is used during the production of the oxygen sensor according to the first embodiment of the invention.
Figure 5:
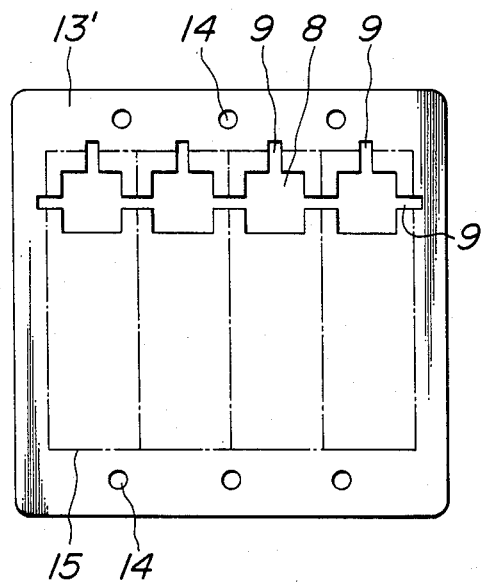
FIG. 5 is a plan view similar to FIG. 4, illustrating a card-shaped body for a plurality of intermediate board members.
Figure 6:
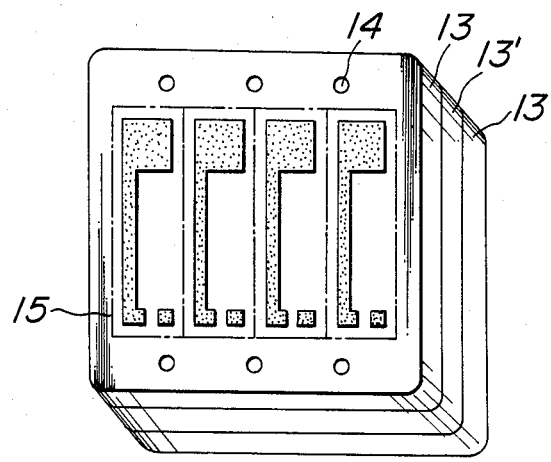
FIG. 6 is a schematic perspective view of a body formed by overlaying the card-shaped bodies of FIGS. 4 and 5 before sintering.

Referring to FIGS. 4 through 6, a method used by the inventors for producing the oxygen sensor according to the first embodiment will be described. Powder of a solid electrolyte material was mixed with 4–15 mol % of powder of a stabilizer, such as yttria ($Y_2O_3$), quick lime (CaO), or magnesia (MgO), and the mixture was kneaded with a binder for doctor blades, and the thus kneaded mixture was shaped into planar green bodies with a certain thickness by a conventional extruding process. Card-shaped bodies 13 and 13' were punched from the planar green bodies in such a manner that each card-shaped body 13 or 13' had a width of about 80 mm and a height of about 60 mm. Six fixing holes 14 for registering, three at the bottom and three at the top, were bored in the card-shaping bodies 13 and 13' by punching. Through holes (not shown) for connecting the isolated outlet portions, such as the outlet portions 3d of FIG. 1, to the corresponding lead wire layers, such as the lead wire layers 3b on the opposite side surface of solid electrolyte board 2, were bored at those portions of the card-shaped body 13 which corresponded to the rear portions of the solid electrolyte boards 2 and 5 upon assembling. Four heat-resisting metallic layers 3 were printed on one card-shaped body 13 with a paste of heat-resisting metal, so as to formulate the electrode layers 3a, the lead wire layers 3b, and outlet portions 3c and 3d. The paste contained, for instance, platinum powder and 0.05–0.30 part by weight, or 0.20 part by weight in the illustrated example, based on the platinum powder, or powder of the same material as that of the solid electrolyte boards. The above-mentioned holes 8 and a passage 9 for four intermediate board members 7 were simultaneously punched out from the other card-shaped body 13', as shown in FIG. 5. Another card-shaped body 13 was punched and provided with the heat-resisting metallic layers 6 in the same manner as the above-mentioned card-shaped body 13 of FIG. 4. The card-shaped body 13' with the holes 8 and the passages 9 bored therethrough was sandwiched between the card-shaped body 13 with the heat-resisting metallic layers 3 and the other card-shaped body 13 with the heat-resisting metallic layers 6 as shown in FIG. 6, and a solvent for the binder used in the above-mentioned shaping was applied thereto so as to bind the three card-shaped bodies 13, 13' and 13, as shown in FIG. 6. The combination of the three card-shaped bodies thus bound was cut along cutting lines 15 as shown by the dash-dot lines of FIG. 6, whereby four green bodies of tri-laminal construction were formed. After removing the binder, the green bodies of tri-laminal construction was fired at 1,400°–1,600° C. for about four hours, and the oxygen sensors as shown in the perspective view of FIG. 2 were produced. If necessary, porous ceramic protective films may be printed only on those surfaces of the electrode layers which are on the outer surface of the oxygen sensor or on the electrode layer surfaces both inside and outside of the oxygen sensor. The ceramic protective films may be made of the same material as those of the above-mentioned planar green bodies or an insulating material such as alumina and spinel. If the ceramic protective films are applied only to the electrode surfaces on the outside of the oxygen sensor, such ceramic protective films may be applied by flame spraying after the firing.

Figure 3:
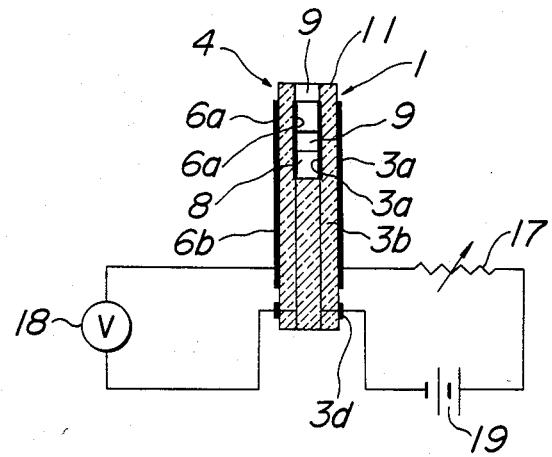
FIG. 3 is a schematic circuit diagram, showing the manner in which the oxygen sensor of the first embodiment is used.

Tests were made on the oxygen sensor of the invention by using an arrangement as shown in FIG. 3. The oxygen sensor was disposed in an exhaust gas pipe (not shown), so as to expose the front portion 11 thereof to the exhaust gas. The cavity at the hole 8 of the intermediate board member 7 had a thickness of 0.5 mm between the oxygen pump element 1 and the oxygen concentration cell element 4, and a cross-sectional area of 100 mm$^2$ taken at right angles to the direction of the thickness, which cross-sectional area substantially corresponded to the area of the electrode layer 3a or 6a of the oxygen pump element 1 or oxygen concentration cell element 4. The cavity communicated with the outside of the oxygen sensor through three passages 9, and each passage 9 had a cross section of 0.5 mm × 2 mm and a length of 1 mm. The electrode layer 3a or 6a as a porous platinum layer with a thickness of 15 μm and a porosity of 30%. The oxygen pump element 1 or the oxygen concentration cell element 4 includes the solid electrolyte board 2 or 5 made of zirconia ($ZrO_2$) partially stabilized with yttria ($Y_2O_3$). A DC voltage of 10 V was applied across the electrode layers 3a of the oxygen pump element 1 through a variable resistor 17, so as to vary the direct current I through the element 1 in a range of 0.05–10 mA for pumping out oxygen from the gas in the cavity at the hole 8 in a controllable fashion. The output voltage of the oxygen concentration cell element 4 was controlled at 20 mV. The inventors found out through the tests that the above-mentioned current I under such conditions corresponded to an oxygen concentration of about 0.05–10% in the gas outside the oxygen sensor or the gas being measured. The relationship between the current I and the oxygen concentration of the gas being measured proved to be linear. During the tests, the temperature of the oxygen sensor was kept at 800° C.

The intermediate board 7 of the oxygen sensor used in the tests was made of the same oxygen-ion-conductive solid electrolyte as those of the solid electrolyte boards 2 and 5 of the oxygen pump element 1 and the oxygen concentration cell element 4. However, it is possible to form the intermediate board member 7 with a ceramic material different from those of the solid electrolyte boards 2 and 5, and for instance, the intermediate board member 7 may be made of alumina or spinel, provided that both the difference in the sintering temperature and the difference in the coefficient of thermal expansion between the intermediate board member 7 and the solid electrolyte board 2 or 5 are not very large.

Figure 7:
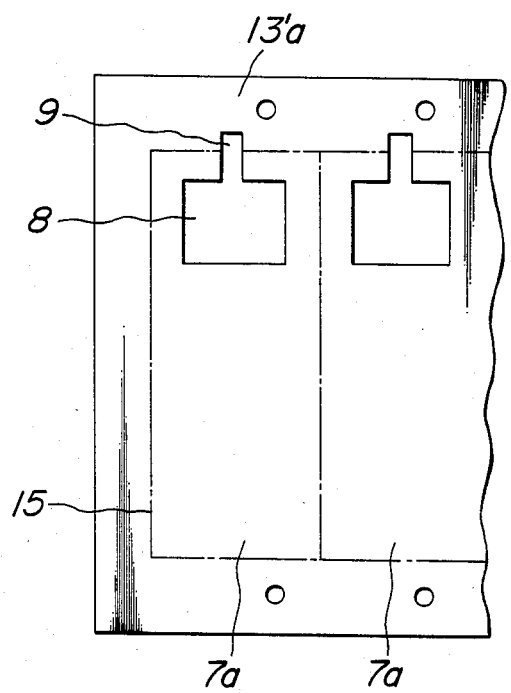
FIGS. 7 and 8 are plan views of card-shaped bodies to be used in producing an oxygen sensor according to a second embodiment of the invention.
Figure 8:
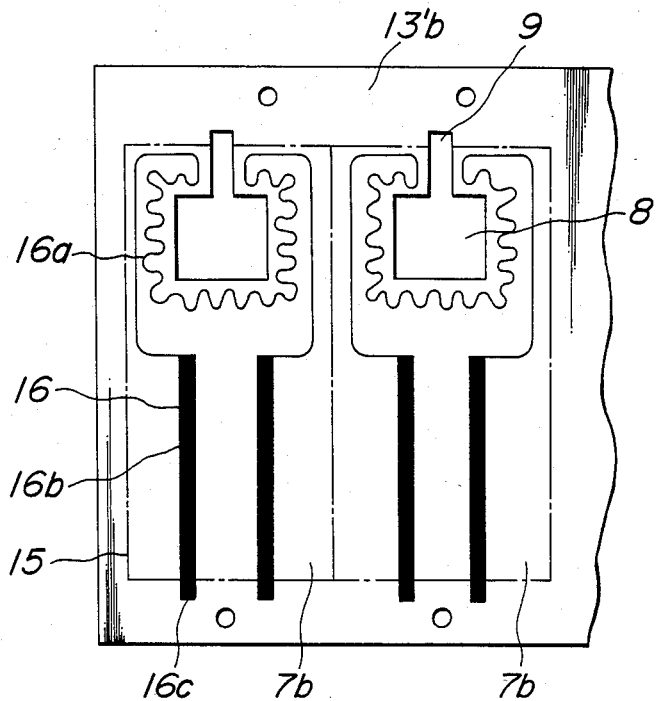
Figure 9:
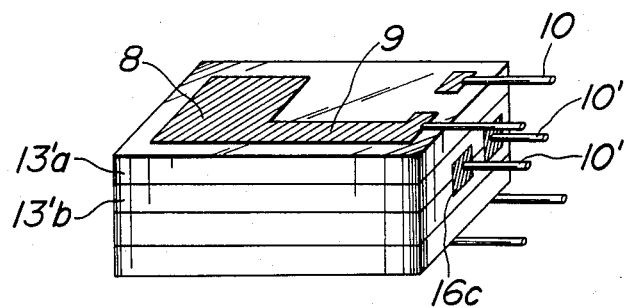
FIG. 9 is an overall perspective view of the assembled oxygen sensor of the second embodiment.

FIG. 7 and FIG. 8 show a second embodiment of the oxygen sensor according to the present invention. In this embodiment, two intermediate board member layers 7a and 7b are used to form the intermediate board member 7, and each intermediate board member layer 7a or 7b has only one passage 9 communicating a hole 8 to the outer peripheral edge thereof. The two card-shaped bodies 13a' and 13b' of FIGS. 7 and 8 correspond to the one card-shaped body 13' of FIG. 5, and the card-shaped body 13a' is overlaid on the card-shaped body 13b' and the thus overlaid bodies 13a' and 13b' are sandwiched between the two card-shaped bodies 13 of FIG. 4. A heat-resisting metallic layer 16 is deposited, for instance by printing, on the surface of the intermediate board member layer 7b so as to form a heat-generating resistor 16a, lead wire layers 16b extending from the opposite ends of the heat-generating resistor 16a to the rear portion of the intermediate board member layer 7b, and outlet portions 16c (FIG. 9) at the rear end of the lead wire layers 6b. The heat-generating resistor 16a may be made of platinum. Referring to FIG. 9 showing a perspective view of the assembled oxygen sensor according to the second embodiment of the invention, outside lead wires 10' are brazed to the outlet portions 16c of the metallic layer 16, which outside lead wires 10' may be made of platinum or the like heat-resisting metal. When a heating electric current is applied to the heat-generating resistor 16a through the outside lead wires 10' connected to the lead wires 16b at the outlet portions 16c, the temperature range in which the oxygen sensor can be used is expanded, and the temperature dependency of the measurement is accurately and efficiently compensated for with a small power consumption.

In short, the oxygen sensor of the present invention measures the oxygen partial pressure in the gas or atmosphere being measured based on the fact that, when a steady balance of the oxygen flow and a steady distribution of the oxygen concentration are established in the oxygen sensor, there is a functional relationship among the oxygen partial pressure in the gas being measured, the electric current through the oxygen pump element for pumping in or pumping out (this current directly relates to the amount of oxygen moving from the above-mentioned enclosed cavity to the gas being measured or vice versa through the oxygen pump element), and the output from the oxygen concentration cell element, which output gives the ratio between the oxygen partial pressure in the above-mentioned enclosed cavity or gap communicating with the gas being measured through the above-mentioned passages and the oxygen partial pressure in the gas being measured, said ratio being determined by the well-known Nernst's equation. Accordingly, the method of the measurement by using the oxygen sensor of the invention is not restricted to the above-mentioned approach of varying the magnitude of the electric current through the oxygen pump element, but the oxygen sensor of the invention can be used by a different method, for instance by allowing the output from the oxygen concentration cell element to vary so as to represent the oxygen partial pressure of the gas being measured under the conditions that the pumping out electric current through the oxygen pump element is controlled at a constant value.

As described in the foregoing, the oxygen sensor of the present invention uses a construction in which an oxygen pump element, an intermediate board member, and an oxygen concentration cell element are overlaid one above the other in said order, and such overlaid elements and board member are united into a unitary oxygen sensor by sintering, while a flat cavity is formed between the two elements, which cavity is communicated with the outside of the oxygen sensor through one or more passages having a cross-sectional height equivalent to the thickness of the cavity, whereby outstanding advantages are achieved in that the risk of performance deterioration due to clogging of oxygen-diffusing holes of said passages is eliminated by using the passage with a large cross section, that a quick response of the oxygen sensor in a practicable range is achieved (for instance, a response time of shorter than 0.5 sec is achieved), that the oxygen concentration can be measured with a comparatively small oxygen-pumping current through the oxygen pump element, and that the oxygen sensor is easy to manufacture and has a high durability.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen sensor, comprising
an oxygen pump element formed of a first oxygen-ion-conductive solid electrolyte board having electrode layers attached to opposite surfaces at one end of the first board and lead wire layers extending from said electrode layers to opposite end of the first board;
an oxygen concentration cell element formed of a second oxygen-ion-conductive solid electrolyte board disposed in parallel to said first board, said second board having electrode layers attached to opposite surfaces at one end thereof in alignment with said electrode layers of said first board and lead wire layers extending from said electrode layers attached thereon to opposite end thereof; and
a ceramic intermediate board member disposed between said oxygen pump element and said oxygen concentration cell element, said intermediate board member having a hole bored therethrough so as to define a cavity by closing said hole with said electrode layers attached to opposite surfaces of the first board and the second board, said cavity having a thickness of 0.1-2.0 mm taken as a spacing between said oxygen pump element and said oxygen concentration cell element, and at least one passage formed through said intermediate board member so as to communicate said cavity to outside of the oxygen sensor, said at least one passage having a cross-sectional area of more than 1 mm² taken at right angles to direction of communication between said cavity and outside of said oxygen sensor and having a cross-sectional height substantially equivalent to the thickness of said cavity; said electrode layers and lead wire layers being metallic layers which are deposited by thick film forming technique.

2. An oxygen sensor as set forth in claim 1, wherein said intermediate board member is made of the same solid electrolyte as those of said first and second boards.

3. An oxygen sensor as set forth in claim 1, wherein said intermediate board member is made of a ceramic material which is different from those of said first and second solid electrolyte boards and which has small difference in sintering temperature and in thermal expansion coefficient between said first and second solid electrolyte boards.

4. An oxygen sensor as set forth in claim 3, wherein said intermediate board member is made of alumina.

5. An oxygen sensor as set forth in claim 3, wherein said intermediate board member is made of spinel.

6. An oxygen sensor as set forth in claim 2 or 3, wherein said intermediate board member has a plurality of said passges, said passages extending in different directions through said intermediate board member.

7. An oxygen sensor as set forth in claim 6, wherein the total of cross-sectional areas of all said passages is more than 1 mm², each of said areas of the passages being taken at right angles to direction of communication between said cavity and outside of the oxygen sensor through related one of said passages.

8. An oxygen sensor as set forth in claim 7, wherein said total of cross-sectional areas of all said passages is more than 3 mm².

9. An oxygen sensor as set forth in claim 6, wherein said electrode layers are made by printing a paste and sintering the thus printed paste at the time of sintering of the related element so that each of the electrode layers has a thickness of 5-20 μm and a porosity of 10-40%, said paste consisting of heat-resisting metal powder and 0.05-0.30 part by weight, based on said heat-resisting metal powder, of powder of material of said first and second boards.

10. An oxygen sensor as set forth in claim 1, wherein said at least one passage has a cross-sectional area of more than 3 mm² taken at right angles to direction of communication between said cavity and outside of the oxygen sensor.

11. An oxygen sensor as set forth in claims 1, 2 or 3 wherein said electrode layers are made by printing a paste and sintering the thus printed paste at the time of sintering of the related element so that each of the electrode layers has a thickness of 5–20 μm and a porosity of 10–40%, said paste consisting of heat-resisting metal powder and 0.05–0.30 part by weight, based on said heat-resisting metal powder, of powder of material of said first and second boards.

12. An oxygen sensor as set forth in claim 1, wherein said at least one passage has a thickness which is the same as the thickness of the cavity.

13. An oxygen sensor as set forth in claim 1, which has an integral structure made by lamination and sintering of the first oxygen-ion-conductive solid electrolyte board, the ceramic intermediate board member and the second oxygen-ion-conductive solid electrolyte board.

* * * * *